(12) United States Patent
Buonamici

(10) Patent No.: US 9,011,841 B2
(45) Date of Patent: Apr. 21, 2015

(54) FLOUR-BASED FUNCTIONAL FOOD

(76) Inventor: Guglielmo Buonamici, Calci (IT)

(*) Notice: Subject to any disclaimer, the term of this patent is extended or adjusted under 35 U.S.C. 154(b) by 0 days.

(21) Appl. No.: 14/110,434

(22) PCT Filed: Apr. 5, 2012

(86) PCT No.: PCT/IB2012/051688
§ 371 (c)(1),
(2), (4) Date: Dec. 20, 2013

(87) PCT Pub. No.: WO2012/137163
PCT Pub. Date: Oct. 11, 2012

(65) Prior Publication Data
US 2014/0105879 A1 Apr. 17, 2014

(30) Foreign Application Priority Data
Apr. 8, 2011 (IT) .................. PI2011A0038

(51) Int. Cl.
| | | |
|---|---|---|
| *A23L 1/30* | (2006.01) | |
| *A21D 2/14* | (2006.01) | |
| *A21D 2/36* | (2006.01) | |
| *A23L 1/10* | (2006.01) | |
| *A61K 31/045* | (2006.01) | |
| *A61K 31/352* | (2006.01) | |
| *A61K 31/366* | (2006.01) | |
| *A61K 36/06* | (2006.01) | |
| *A61K 36/48* | (2006.01) | |
| *A61K 36/899* | (2006.01) | |
| *A61K 36/28* | (2006.01) | |
| *A61K 31/122* | (2006.01) | |
| *A61K 31/575* | (2006.01) | |

(52) U.S. Cl.
CPC .............. *A23L 1/3004* (2013.01); *A21D 2/14* (2013.01); *A21D 2/36* (2013.01); *A23L 1/1016* (2013.01); *A23L 1/3002* (2013.01); *A23L 1/3016* (2013.01); *A23L 1/3018* (2013.01); *A61K 31/045* (2013.01); *A61K 31/352* (2013.01); *A61K 31/366* (2013.01); *A61K 36/06* (2013.01); *A61K 36/48* (2013.01); *A61K 36/899* (2013.01); *A61K 36/28* (2013.01); *A61K 31/122* (2013.01); *A61K 31/575* (2013.01)

(58) Field of Classification Search
IPC .............. A23L 1/3004,1/1016, 1/3018, 1/3002, A23L 1/3016; A21D 2/14, 2/36; A61K 31/352, A61K 31/366, 31/122, 31/575, 31/045, 36/06, A61K 36/48, 36/899
See application file for complete search history.

(56) References Cited

U.S. PATENT DOCUMENTS

| | | | |
|---|---|---|---|
| 2006/0165671 A1* | 7/2006 | Raederstorff et al. | 424/94.1 |
| 2009/0232916 A1* | 9/2009 | Shulman et al. | 424/752 |
| 2010/0034926 A1* | 2/2010 | Frick et al. | 426/61 |

* cited by examiner

*Primary Examiner* — Rosanne Kosson
(74) *Attorney, Agent, or Firm* — R. Ruschena Patent Agent, LLC

(57) ABSTRACT

The invention relates to a functional flour-based food composition, in particular baked products, and a method for the preparation thereof. Specific substances of vegetable origin principally containing policosanols, isoflavones and vegetable statins are added to the flour, or to the dough for preparing the aforesaid baked products. Further components can be added to the preparation in order to enhance the effectiveness and sensory qualities thereof. The functional food composition of the invention favors the re-balancing of cholesterol and triglyceride values.

19 Claims, No Drawings

FLOUR-BASED FUNCTIONAL FOOD

RELATED APPLICATIONS

This application is the U.S. National Stage under 35 USC 371 of PCT Application PCT/IT2012/051688 with International Filing Date of Apr. 5, 2012.

BACKGROUND OF THE INVENTION

1. Field of the Invention

The present invention relates to a food composition based on an edible flour, prevalently from cereals, to which substances of vegetable origin containing various active ingredients are added and which is mainly intended to exert an action of stabilizing the cholesterol and triglyceride levels in the human body.

2. Brief Description of the Prior Art

SUMMARY OF THE INVENTION

The present invention also relates to a method for preparing a functional food composition, in particular pasta or baked food products, having an action of stabilizing cholesterol and triglyceride levels and prepared from a flour-based dough and comprising specific substances of vegetable origin. Cholesterol is a steroid, i.e. a lipidic molecule consisting of four polycycloaliphatic rings (condensed together in a trans-formation) and an aliphatic tail, in addition to any functional groups present. Cholesterol is an essential ingredient of the cell membrane of all animal cells. Together with protein molecules, cholesterol regulates the exchange of messenger substances through the cell membrane. Cell growth and division are not possible without cholesterol. When we speak of "cholesterol" in medicine, we do not mean chemical cholesterol (this is a simplifying ambiguity), but are rather talking about a class of lipoproteins (chylomicrons, transport aggregates) which circulate in the blood: the concentration thereof is called blood cholesterol.

Based on recommendations of the World Health Organization (WHO), for several years a distinction has been made in cholesterol analysis between: total blood cholesterol, which should be below 200; and total blood cholesterol/HDL ratio, not to exceed 5 for men and 4.5 for women. When there is an excess of cholesterol in the blood, one can speak of hypercholesterolemia; more precisely, this refers to an increase in the cholesterol transported by low-density lipoprotein (LDL), commonly defined as "bad cholesterol".

Like all lipids, cholesterol is not water soluble, so that its transport in the blood is mediated by proteins called apolipoproteins (APO). The complex formed by apolipoproteins, cholesterol, triglycerides and phospholipids constitutes lipoproteins, relatively voluminous particles which circulate in the blood in order to transport fats toward all tissues. Under fasting conditions (that is, when the test is performed), the cholesterol present in the blood is mostly (60-75%) LDL transported, so lo that the assay of total cholesterol in plasma is an indicator, albeit an approximate one, of LDL cholesterol. However, since a good percentage of cholesterol is also transported by other lipoproteins (VLDL and HDL), for a more exact evaluation of blood cholesterol it is preferable to assay the LDL. This method enables LDL cholesterol ("bad" cholesterol) to be distinguished from HDL cholesterol ("good" cholesterol). LDL (which is a metabolic product of the VLDL synthesized in the liver) transports cholesterol from the liver to tissues, where it is used for a variety of processes; however, when LDL is present in excessive concentrations, its accumulation in arterial walls promotes the development of atherosclerosis. Consequently, LDL hypercholesterolemia represents one of the largest risk factors for cardiovascular disease. HDL, on the contrary, is responsible for the "reverse transport" of cholesterol, i.e. it removes excess cholesterol from tissues and transports it to the liver. From here it is eliminated in the intestinal lumen, in part as bile salts and in part as free cholesterol. HDL thus performs a protective function against the development of cardiovascular diseases. A high value of HDL cholesterol is therefore a favourable factor.

Several substances of vegetable origin are capable of exerting action on total blood cholesterol and on the total cholesterol/HDL ratio. Policosanols are a mixture of phytomolecules consisting of high molecular weight aliphatic alcohols extracted prevalently from *Saccharum oflicinarurn* (sugar cane), but also from other vegetable substances, such as *Medicago sativa* (alfalfa). The principal molecules are Octacosanol, Tetracosanol and Hexacosanol. Octacosanol is contained in the aforesaid plants, in cotton and in the waxy layer of the leaves of a variety of plants, and can also be found in significant quantities in wheat germ oil. Policosanols can also be produced synthetically, but not being accompanied by other phytocompounds normally present, they are less lo effective than natural ones. In nature, for example, octacosanol is always accompanied by and synergistic with vitamin E and B group vitamins, as well as minerals.

Policosanols have the property of lowering "bad" cholesterol (LDL) by reducing an enzyme at the basis of its production (Prat H. et al., 1999), and the percentage of triglycerides (Mas R. et al., 1999), as well as performing an anti-aggregating action in blood (Mas R. et al., 1998; Arruzazabala M. L. et al., 2002; Castano G., Mas R., Fernandez J. C. et al., 2001), thus reducing the risk of obstructions forming in blood vessels. Policosanols also have important antioxidant functions and are thus effective in combating free radicals and hindering LDL oxidation, which can represent the main cause of atherosclerotic manifestations.

The numerous clinical studies published to date (Gouni-Berthold I. et al., 2002) indicate that a dose of policosanols ranging between 10 and 20 mg/days is capable of lowering total cholesterol by 17 to 21% and LDL cholesterol by 21 to 29%, as well as increasing HDL cholesterol by between 8 and 12%; moreover, policosanols also bring about an average 10% reduction in triglycerides. Recent studies confirm that policosanols display the same effectiveness as simvastatin and pravastatin in reducing cholesterol (Ortensi G., Gladstein J., Valli H. et al, 1997). Further studies (Castaño G. et al, 2003) have demonstrated that the effectiveness of policosanols in reducing cholesterol is only slightly lower than that of atorvastatin.

Isoflavones are natural chemical compounds belonging to the phenolic compounds of vegetable origin which in turn belong to the broader class of flavonoids. Isoflavones are present in the Leguminosae and Iridaceae and in particular they are concentrated in the Papilionideae, subfamily of the Leguminosae, and are thus found in foods such as chick peas, whole grain cereals, beans, fava beans, fennel, lentils, soybean and red clover. Several clinical studies (Zhuo X. G. et al., 2004; Mosca G., 2008; Zhan S. et al., 2005) have highlighted the effects of soy protein and the isoflavones contained in it on cholesterol and triglycerides and it was shown that soy protein containing isoflavones exerted a significant action in reducing total cholesterol, LDL (low-density lipoprotein) cholesterol and triglycerides, along with an action of increasing HDL (high-density lipoprotein) cholesterol (good cholesterol). The reduction effect demonstrated to be greater the higher the cholesterol level was prior to the therapy. From a structural and functional viewpoint, isoflavones are similar to the estrogen produced by the body and have the property of binding to the same receptors. For this reason they are commonly called phytoestrogens; among them, one of the most important and studied, being considered to date the most biologically active one, is genistein and the respective bglucoside of genistein. In soy-based foods, the glucosidic form can be found, even though the bio-active form is represented by the isoflavone devoid of glucose, namely, aglycone. Therefore, the natural isoflavones of soy must be activated by hydrolysis of the glucosidic group in order to acquire their biological functionality.

In the gastroenteric tract there are enzymes called b-glucosidases which intervene in the action of detaching glucose, transforming the glucose molecule into the active form called aglycone; in this form it can be absorbed at the intestinal level. The aglycone is structurally similar to estrogens and can thus bind to the same receptors. In humans, two different estrogen receptors have been identified, called ERa and ERb (Bitto A., 2010). Vis-à-vis these receptors a different and very interesting binding activity is exhibited by phytoestrogens, in particular genistein; in fact, genistein possesses a high affinity for ERb, similar to that of estrogen, and 20 times greater than the affinity for the receptors ERa.

This differentiated action of genistein gives rise to an original profile of lo safety and effectiveness; the effectiveness can be explained with reference to genistein's high affinity for b type estrogen receptors (ERb), which are abundant in the cardiovascular system.

Statins (pravastatin, atorvastatin, cerivastatin, fluvastatin) are among the most effective drugs for reducing total blood cholesterol and LDL. Statins act at the origin of the problem, by limiting the synthesis of endogenous cholesterol.

In particular, these drugs block the activity of an enzyme called HMG-CoA reductase (Hydroxy-Methyl-Glutaril-Coenzyme A-reductase), which is fundamental in the processes of cholesterol synthesis, especially in the liver.

Another big advantage of statins resides in their selectivity, that is, in their ability to reduce above all the synthesis of "bad" cholesterol (LDL), leaving the "good" cholesterol practically unchanged (HDL). Statins are moreover endowed with interesting anti-inflammatory properties, which protect the walls of the vessels, stabilizing atheromatous plaque and reducing the risk of occurrence of an adverse event, such as a heart attack, angina pectoris or sudden rupture of an aneurism. Despite their enormous therapeutic effectiveness, statins are not devoid of side effects, which above all affect the liver.

Alterations of liver function and muscular pains are among the most common unwanted effects. For this reason, the use of statins is contraindicated in alcoholics, during pregnancy and breastfeeding, in children and in patients with hepatic dysfunctions. There also exist natural statins of vegetable origin, which, unlike synthetic statins, have no contraindications to their use or demonstrated side effects. Vegetable statins include, for example, monacolins, which perform a marked and demonstrated hypocholesterolemic action. Standing out among them is monacolin K, which mirrors the chemical structure and pharmacological lo action of lovastatin (a drug belonging to the category of statins). Like these pharmaceutical products, monacolin K is capable of inhibiting HMG-CoA reductase, which represents a key enzyme in the biosynthesis of cholesterol. Monacolins are found in abundance in fermented red rice, which is obtained from the fermentation of common cooking rice (*Oryza sativa*) by a particular yeast called *Monascus purpureus* or red yeast. There are known food compositions specifically conceived for problems of obesity, and in particular for reducing the concentration of cholesterol, which exploit the action of some of the substances of vegetable origin described above.

For example, WO200906999 A1 discloses a food composition based on soy, rice and sesame which is indicated in cases of obesity and capable of reducing cholesterol and triglyceride levels. The aforesaid food composition can be in the form of a food supplement or a complete food. US 201010298261 A1 discloses a food composition able to reduce total cholesterol and in particular LDL cholesterol levels. The aforesaid food composition is based on dietary fibres, in particular beta-glucan, and plant sterols and/or plant stanols in a free and esterified form. US 200910285922 A1 discloses a flour-based food product containing Opuntia ficus-indica, which should be capable of combating obesity by reducing the concentration of LDL cholesterol, lipids and glucose. US 2009/0017099 A1 discloses a composite food that comprises a portion of a cholesterol-rich food such as a hamburger or hot dog and a baked product, for example a bun, comprising a sufficient amount of phytosterols to compensate for the cholesterol contained in the hamburger or hot-dog. None of the above-mentioned patents use the synergistic action of the described vegetable substances which have a demonstrated hypocholesterolemic action.

The inventor guessed that an association of policosanols, phytosterols and isoflavones, as well as other specific substances of vegetable origin, mixed lo and prepared in a food flour-based composition, in particular pasta or baked products, would be particularly synergistic and effective for stabilizing cholesterol and triglyceride levels.

DETAILED DESCRIPTION OF THE INVENTION

The principal object of the present invention is to provide a flour-based food composition comprising vegetable substances that are useful for stabilizing cholesterol and triglyceride levels. A further object of the present invention is to provide a method for preparing baked food products which are capable of exerting an action of stabilizing cholesterol and triglyceride levels.

The flour used as the base of the food composition of the invention is cereal flour. Preferably, a soft wheat flour is used. The term flour is meant to refer both to pure wheat flour, corresponding to milled wheat, and the wheat flour-based food composition comprising other types of edible flours and/or chemical additives, also called "improvers", which are mainly useful for improving the bread-making process. Among the various substances that can be added we find, for example, malt flour, soy flour, L-ascorbic acid, enzymes, emulsifiers such as esters of mono- and diglycerides, dextrose, sucrose, alpha- and beta-amylase, stabilizers such as guar seed flour, and still others.

The food composition of the present invention can consist exclusively of flour and the specific vegetable substances that exert the hypocholesterolemic action, or else it can be a dough for preparing baked food products also comprising water, salt, leavening, and still other substances.

In addition to the phytosterols, isoflavones and policosanols mentioned above, further substances derived from plant species can be advantageously added to the functional food composition of the present invention.

Plant sterols, or phytosterols, are molecules of a sterolic nature present in plants; they in fact make up part of plant cell membranes. About 40 phytosterols are known; the phytosterols most present in the diet are betalo sitosterol (50%), campesterol (33%) and stigmasterol (4%). As may be noted from the percentages, the other phytosterols are present in very modest amounts. Beta-sitosterol differs from cholesterol because of the ethyl group at position 24 of the side chain. It is by now well-established that phytosterols are effective against high blood cholesterol. Their mechanism of action is very simple: phytosterols decrease the cholesterol levels in blood by reducing intestinal cholesterol absorption. This mechanism is based on the substitution of cholesterol inside micelles, which are veritable means of transport for cholesterol. Given that micelles have a limited capacity to incorporate phytosterols, the concentration of cholesterol in the same is reduced and, accordingly, less is absorbed through the intestinal membrane. The cholesterol not incorporated into the micelles forms co-crystals with the phytosterols and together they are eliminated through faeces. Phytosterols, unlike cholesterol, are not capable of producing atherosclerotic plaques. In the diet, they are found especially in vegetable oils, nuts and some seeds and legumes. One particularly interesting source of phytosterols is a plant of the family Cucurbitaceae, whose scientific is *Cyclanthera pedata*. The clinical studies conducted demonstrate that *Cyclanthera pedata* helps to reduce blood cholesterol levels. Through its use it is possible to achieve an 18% reduction in total cholesterol levels and a 23% reduction in bad cholesterol or LDL, with the additional advantage of raising the level of good cholesterol or HDL by up to 42%. In the composition of Caigua (one of the common names of *Cyclanthera pedata*) there are many elements which explain these anticholesterol effects. The best known are phytosterols such as sitosterol-3-5 beta-D-glycoside.

Saponins, or saponin glycosides, are complex molecules characterized by an aglycone structure of a steroidic or triterpenic nature. They are responsible for a cholesterol lowering activity thanks to which total cholesterol and LDL cholesterol are significantly reduced. They are found, lo for example, in *Glycine max* and *Medicago sativa* extracts. Folic acid, or pteroyl(mono)glutamic acid or vitamin B9, exerts an action of limiting homocysteine, which is a sulphur-containing amino acid that forms following the enzymatic transformation of methionine, another sulphurated amino acid present in proteic foods (dairy products, meat, legumes, eggs) and which can prove even more harmful than cholesterol. Folic acid is contained, for example, in *Medicago sativa* extracts. Coenzyme Q10, also called ubiquinone, or vitamin Q, is an organic molecule, and more precisely a benzoquinone with very long isoprene side chain. This coenzyme, ubiquitous in biological systems, displays a structure similar to that of vitamin K and vitamin E. It is found in abundance in soybeans, cereals, walnuts and grapes. In organisms, it participates in redox reactions. It possesses a strong scavenger action and for this reason protects cellular structures against free radicals. It performs its action synergistically with vitamin E, protected in turn by coenzyme Q10, which assures the bond thereof with octacosanol; the latter, in turn, is also bonded to B group vitamins and minerals. This coenzyme is in fact a water-insoluble lipophilic compound with adjuvant action in the transport of electrons and in mitochondrial energy production. The intake of coenzyme Q10 can exert cardioprotective, cytoprotective and neuroprotective effects; it also performs an action of inhibiting the oxidation of LDL cholesterol, which is believed to be the largest pathogenetic component of atherosclerosis. (Littaru G. P. & Tiano L., 2005; Linnane A. W. et al., 2002; Mizuno M. et al., 1997; Niklowitz P. et al., 2002).

The levels thereof in the human body decrease with advancing age, perhaps because of a decrease in its synthesis or because of the increase in lipid peroxidation which occurs with age.

Cynarin is an active ingredient contained in the cauline leaves of the common artichoke (*Cynaria scolymus*).

It chemically derives from the condensation of two units of caffeic acid with a molecule of quinic acid (1,4-dicaffeilquinic acid). In clinical studies, artichoke extracts have shown to improve choleresis and the symptoms of patients suffering from dyspepsia and functional disorders of the liver. Cynarin has shown to be effective as a hypolipidemic remedy in a number of clinical studies. Cynarin seems to stimulate bile secretion by liver cells and increase the excretion of cholesterol and solid matter in bile. Caffeic acid derivatives in general show antioxidant and hepatoprotective effects. Cynarin is also hypocholesterolemic, by virtue of its inhibition of cholesterol biosynthesis and inhibition of LDL cholesterol oxidation. Moreover, it decreases the betalalpha quotient of lipoprotein and has diuretic effects.

The substances specified above, which have a specific hypocholesterolemic action, can also have various types of vitamins or minerals added to them. A food composition containing a combination of the above-mentioned substances, blended in the right doses, has numerous nutritional advantages: it favours the stabilization of cholesterol on correct levels; it exerts an antioxidant action; it has an organic anti-oxidative stress action; it acts to protect the liver; it protects arteries and the cardio-circulatory system in general; and it reduces risk of stress-induced avitaminosis. All of the above-described substances are of vegetable origin and are advantageously obtained from extracts of specific plant species which contain one or more of the aforesaid substances. Sugar cane (*Saccharum officinarum* L.) is a tropical plant, native to Indo-Malaysian regions and belonging to the family Poaceae. Policosanols, in particular octacosanol, are extracted from sugar cane wax, a byproduct of sugar production.

Fermented red rice, as already mentioned, is obtained through the fermentation of common cooking rice (*Oryza sativa*) by a particular yeast, lo called *Monascus purpureus* or red yeast. During its fermenting activity, this yeast in fact becomes enriched with a group of substances, called monacolins, to which a marked hypocholesterolemic activity has been scientifically attributed. It has been demonstrated that fermented red rice is more effective in terms of hypocholesterolemic action than equivalent doses of lovastatin, evidence that its properties reflect a combination of actions that are not ascribable to monacolin K alone. For this reason as well, in addition to its well-documented hypolipidemic activity, fermented red rice seems to reduce cardiovascular risks thanks to anti-atherosclerotic actions of another type (anti-inflammatory and vasodilating effects and reduction of lipoprotein A levels). Moreover, fermentation controlled in a laboratory can slightly vary the composition of the *Monascus purpureus* and enable the selection of strains rich in monacolin K or in other substances endowed with particular pharmacological actions. Unlike in the case of synthetic statins (considered veritable drugs), the use of fermented red rice extracts is also allowed in the production of food supplements, provided that it remains within certain limits established by the Ministry.

Soybean, soy or soya (*Glycine max* L.) is a herbaceous plant of the family of Leguminosae, native to East Asia. The part used is the seeds, which contain a high amount of protein, polyunsaturated lipids and glucosides, including isoflavones and saponins. Soybean is a leguminous plant like beans, chick peas or lentils, and like all legumes it is rich in B group vitamins, coenzyme Q10, iron and potassium. However, soybeans are more digestible and richer in protein and lipids (monounsaturated and polyunsaturated and phospholipids like lecithin) than other legumes. Soy protein has a quite good amino acid profile with a biological value of less than 75, and a protein efficiency ratio of 2.1.

*Medicago sativa* L., known as alfalfa (from the Arabic al-fal-fa, "father of all foods"), is a herbaceous plant belonging to the family Fabaceae (or lo Leguminosae). It contains 8 digestive enzymes, phytoestrogens, 40 different bioflavonoids (with antioxidant, anti-inflammatory and blood vessel reinforcing action), flavones, glucosides, alkaloids (a support to antibiotic activity and anti-inflammatories, they favour protein formation), amino acids, vitamin A, vitamin B9, vitamin C, vitamin D, vitamin E, vitamin K, minerals, trace elements and high quantities of chlorophyll. Caigua is a plant native to Peru and belongs to the family Cucurbitaceae. Its scientific name is *Cyclanthera pedata*, but it is found under many other names: Achocha, Achokcha, Caihua, Caygua, Cayua, Caigua, Korila etc. Its genus comprises around forty indexed species. The fruit contains peptin, galacturonic acid, dihydroxytryptamine, resins, minerals such as phosphorous, vitamin C, lipoprotein (sitosterol-3-beta-D-glucoside) and spheroidal components with a hypoglycaemic and anti-LDL cholesterol action.

The artichoke (*Cynara cardunculus* L. ssp. *scolymus* L.) is a plant of the family Asteraceae, cultivated in Italy and in other countries for use as a food and, secondarily, for medicinal use. The main component of artichokes, after water, is carbohydrates, among which a distinction is made between inulin and fibres. The main minerals are sodium, potassium, phosphorous and calcium. Among vitamins, there is a prevailing presence of B1 and B3 and small amounts of vitamin C. What is more important in explaining the pharmacological activity of artichoke extracts is the presence of a complex of characteristic secondary metabolites: caffeic acid derivatives, including chlorogenic acid, neochlorogenic acid, cryptochlorogenic acid and cynarin; flavonoids, in particular rutin; and sesquiterpene lactones: among others, cynaropicrin, dihydrocynaropicrin, grossheimin and cynaratriol.

With a functional flour-based food composition containing substances extracted from the above-described plant species, pasta or baked products such as bread, toasting bread, biscuits, crackers, breadsticks, focaccia and lo still others, are advantageously prepared according to the method of the present invention, capable of stabilizing cholesterol and triglyceride levels. According to the present invention, the above-described objects are achieved thanks to the solution specifically referred to in the claims that follow. In relation to the invention, the claims form an integral part of the technical teaching provided.

The invention is illustrated in detail below through examples of nonrestrictive embodiments.

Example 1 a flour-based functional food composition comprises:

| | |
|---|---|
| *Saccharum officinarum* (dry extract titrated to 60% octacosanol). | 34 mg |
| red rice fermented by *Monascus purpureus* (dry extract titrated to 1.5% plant statins). | 750 mg |
| *Glycine max* (dry seed extract titrated to 10% isoflavones) | 500 mg |
| *Medicago sativa* (alfalfa dry extract) | 50 mg |
| *Cyclanthera pedata* (dry fruit extract titrated to 35% sterolic fraction) | 58 mg |
| *Cynaria scolymus* (dry leaf extract). | 1 g |
| wheat flour | 100 g | where all of the above components are in dry powder form.

Example 2

A method for preparing a baked food product envisages the preparation of a dough which comprises:

| | |
|---|---|
| *Saccharum officinarum* (dry extract titrated to 60% octacosanol). | 2.3 g |
| red rice fermented by *Monascus purpureus* (dry extract titrated to 0.4% monacolin) | 10 g |
| *Glycine max* (dry seed extract titrated to 10% isoflavones) | 35 g |
| *Medicago sativa* (alfalfa juice concentrate). | 3.5 g |
| *Cyclanthera pedata* (dry fruit extract titrated to 35% sterolic fraction) | 4 g |
| *Cynaria scolymus* (dry leaf extract) | 50 g |
| water | 250 ml |
| *Saccharomyces cerevisiae* (baker's yeast) | 7 g |
| Sodium chloride | 5 g |
| Powder bread improver (containing wheat flour, malt flour, emulsifier E472e, enzymes, treatment agent E300) | 3.75 g |
| wheat flour | 750 g | where the ingredients are added in a kneader which mixes the dough for about 30 minutes. The kneading step is followed by a first rising step, after which the dough is formed into loaves. Then follows an additional rising step, after which there is a baking step carried out by placing the loaves in an oven maintained at a temperature of between 180" and 200° C. for a period of time ranging between 30 and 45 minutes. During the kneading step, the wheat proteins gliadin and glutenin are joined together to form gluten. As the kneader works, the gluten is disposed in such a way as to form an ordered meshwork interwoven with starch granules. Cross-linked meshes are thus formed and the air bubbles subsequently containing carbon dioxide produced by fermentation remain trapped in them. The elastic mesh structure does not allow gas to escape and brings about an increase in the dough volume (rising). The kneader operates in such a way as to alternate periods of kneading with periods of rest in order to enable hydration and gluten formation. The kneading step can also take place in a different way than as described above. For example, an alternative kneading method envisages a first step of kneading about 114 to 113 of the total wheat flour with all the baker's yeast and part of the water necessary; after the first kneading, there is a first rising step, after which one adds the rest of the flour, water, salt and other ingredients of the food composition of the invention and proceeds to a second kneading step. This method favours development of the leavening, which acts more rapidly, and makes it possible to use a smaller amount of leavening.

Another variant embodiment of the method for producing the baked products of the invention envisages the use of natural leaven, also called lo sourdough or starter, in the place of baker's yeast. This is a flour and water dough acidified by a complex of yeast and lactic bacteria which are capable of starting fermentation. Unlike baker's yeast, natural leaven comprises, among the leavening agents, different species of heterofermenting and homofermenting lactic bacteria of the genus *Lactobacillus*. The fermentation of lactic bacteria produces organic acids and also enables greater rising of the product and better digestibility and preservability. Some information and definitions regarding the plant species used in the above-described examples of compositions are provided below.

| Fermented red rice | x 100 g |
|---|---|
| glucides | 60 g |
| proteins | 8.8 g |
| Lipids | 2.75 g |
| Fibre | 1.04 g |
| Ash | 2.21 g |
| Amylose | 21 g |

| *Glycine max* | x 100 g of seed extract |
|---|---|
| contains isoflavones (genistein, daidzein), coenzyme Q10 | |
| proteins | 13.1 g |
| lipids | 6.7 g |
| carbohydrates | 9.6 g |
| fibre | 1.1 g |
| water | 69 g |
| ash | 1.59 g |
| potassium | 484 mg |
| phosphorous | 174 mg |
| calcium | 67 mg |
| sodium | 14 mg |

| *Medicago sativa* | x 100 g of dry extract |
|---|---|
| contains isoflavones (genistein, daidzein), policosanols, saponins, lcoumarins, folic acid | |
| proteins | 26 g |
| lipids | 0.2 g |
| polysaccharides | 61 g |
| crude fibre | 23.7 g |
| starch | 4.9 g |
| lignin | 12.3 g |
| ash | 9.3 g |
| nitrogen-free extractives | 37.9 g |
| CaO | 2.56 g |
| $P_2O_5$ | 0.79 g |

| *Cyclanthera pedata* | x 100 g of dry fruit extract |
|---|---|
| proteins | 39 g |
| fibre | 16 g |
| minerals | 10 g |
| betasitosterol and other steroidal saponins | 35 g |

| *Cynaria scolymus* | x 100 g of dry extract |
|---|---|
| water | 86 g |
| proteins | 2 g |
| lipids | 0.2 g |
| glucides | 2.5 g |
| vitamins: B 1, B2, PP, C, Prov.A, E | |
| Minerals: potassium, sodium, calcium, phosphorous, copper, iron, zinc. | |

Example 3

Experimental Data

Functional foods (bread and other baked products) were formulated in which phytocomplexes according to the present invention were combined in different fractions. The same were tested on guinea pigs in order to verify whether and to what extent the added phytocomplexes are capable of lo exerting a favourable action in controlling the lipidemic values of the guinea pigs.

The phytocomplexes added to the foods were the following:
Saccharum officinarum
Oryza sativa
Glycine max
Medicago sativa
Cynara scolymus The results demonstrate that, when they are added to a food like bread, these phytocomplexes are capable of exerting a significant synergistic action in the functional action of the bread itself. The new functional food contains numerous substances capable of exerting an antioxidant action. In particular, it contains: polyphenols, isoflavones, and the *Oryza sativa* ferment (which synergistically inhibit hepatic cholesterol synthesis).

Moreover, the new functional food also contains *Medicago sativa*, which is able to contribute vitamin B9 or folic acid.

Folic acid is essential for the synthesis of several amino acids, the synthesis of purine and pyrimidine, and the reproduction and growth of cells, in particular the erythrocytes in blood.

In this regard, the experimental data showed that *Medicago sativa* extract, included in the formulation of the new functional food (bread), performs an action that is synergistic with that of monacolin k (the vegetable statin formed by *Monascus purpureus* added to the formulation of the functional bread), as it intervenes in decreasing homocysteine, which is increased as a result of the inhibition of the enzyme HMG-CoA reductase, induced, in turn, by the action of the monacolin k that forms during the fermentation of *Oryza sativa*.

Homocysteine is an amino acid that has drawn great interest from the lo medical scientific community, since an excess thereof can be very dangerous for the body's health.

In fact, hyperhomocysteinemia is considered a major independent risk factor which predisposes to cardiovascular pathologies (atherosclerosis, myocardial infarction), cerebrovascular pathologies (stroke) and peripheral vascular pathologies (arterial and venous thrombosis). It is estimated that individuals affected by hyperhomocysteinemia have double the probability of experiencing vascular incidents compared to those who have values within the range of normality.

Moreover, the experimental data obtained showed that, by virtue of its octacosanol content, the *Medicago sativa* extract present in the formulation is capable of performing an action of significantly reducing LDL cholesterol, by an extent ranging from 19 to 29%. The greatest action, in the range of 24-29%, is obtained if it is added to the bread formulation in a form integrated with red rice—*Monascus purpureus*.

The data also demonstrated that:
the bread formulation as described above, in a form supplemented with *Glycine max* extracts, is capable of performing an action of controlling triglycerides and significantly increasing HDL cholesterol;
choline exerts an action synergistically with *Monascus purpureus* and octacosanol, intervening as a coenzyme of metabolism, like B group vitamins, and participating together with inositol in lecithin formation. Like choline, inositol, precisely, is one of the constituents of lecithin, participating in its production in the body. Inositol takes part in fat metabolism, with a synergistic action associated with *Monascus purpureus*, thus contributing to reducing cholesterol in the blood. Furthermore, when integrated with choline, it prevents fats from hardening in the arteries.

Further experimental data obtained demonstrated that:
octacosanol acts directly on the enzyme HMG-CoA reductase, reducing the quantity thereof and thus bringing about a lower production of cholesterol, which is thus inhibited by the enzyme itself;

*Cynara scolymus*, when integrated into the bread formulation, is capable of exerting an action on choleretic activity, synergistically with Trifolium repens and *Medicago sativa*, by virtue of the organic acids present in it and cynaropricrin, which perform a hypolipidemic action, with an increase in cell-surface receptors for LDL and apolipoproteins A1 and A2 synthesized by the liver, and also of bringing about an increase in HDL. Therefore, the functional bread to which vegetable extracts have been added according to the present invention is capable of exerting a functional, salutary action in prevention and treatment of cholesterol and triglyceride levels exceeding the reference values, in addition to an action of protecting the arteries and the cardio-circulatory system and a hepatoprotective and antioxidant action, thanks to the synergistic biochemical actions of the phytocomplexes included in the bread, which enable an enhanced bioactivity thereof to be obtained in the resulting product.

REFERENCES

Canetti M et al. "A two-year study on the efficacy and tolerability of policosanol in patients with type I1 hyperlipoproteinaemia." Int J Clin Pharmacol Res 15(4): 159-65, 1995.

Mas R et al. "Effects of policosanol in patients with type II hypercholesterolemia and additional coronary risk factors." Clin Pharmacol Ther 65(4):439-47, 1999.

Castano G et al. "Effects of policosanol in older patients with type I! hypercholesterolemia and high coronary risk." J Gerontol A Biol Sci Med Sci 56(3):M186-92, 2001.

Castano G et al. "Effects of policosanol on older patients with hypertension and type I1 hypercholesterolaemia." Drugs R D 3(3): 159-72, 2002. Gouni-Berthold the et al. "Policosanol: clinical pharmacology and lo therapeutic significance of a new lipid-lowering agent." Am Heart J 143(2): 356-65, 2002.

Castano G et al. "Effects of policosanol and pravastatin on lipid profile, platelet aggregation and endothelemia in older hypercholesterolemic patients." Int J Clin Pharmacol Res 19(4): 105-16, 1999. Castano G et al. "Comparison of the Efficacy and Tolerability of Policosanol with Atorvastatin in Elderly Patients with Type I1 Hypercholesterolaemia." Drugs Aging 20(2): 15 3-63, 2003.

Arruzazabala, M. L.; Carbajal, D.; Mas, R. et Al., "Cholesterol-lowering effects of policosanol in rabbits", Biol. Res., 1994, 27, 205-8 Arruzazabala, M. L.; Valdes, S.; Mas, R. et Al., "Effect of policosanol successive dose increases on platelet aggregation in healthy volunteers", Pharmacol. Res., 1996, 34, 181-5

Wang J J, et al. "Improvement of monacolin K, gama-aminobutyric acid and citrinin production ratio as a function of environmental conditions of *Monascus purpureus* NTU 601." J Ind Microbiol Biotechnol 2003; 30: 669-76.

Prasad G V R, et al. "Rhabdomyolysis due to red yeast rice (*Monascus purpureus*) in a renal transplant recipient." Transplantation 2002; 74: 1200-1201.

Ma Hallikainen, E S Sarkkinen, M I Uusitupa "Plant stanol esters affect serum cholesterol concentrations of hypercholesterolemic men and women in a dose-dependent manner" 2002.

R Korpela, J. Tuomilehto, "Safety aspects and cholesterol-lowering efficacy of low fat dairy products containing plant sterol" European Journal of Clinical Nutritio 2006.

X Ganrong, C. Yue, L. Xiaorong, L. Xing "Production of Monacolin K in Solid-state fermentation of *monascus* sp. 9901 that does not produce citrinin". lo Endo "Monacolin k, a new hypocholesterolemic agent that specifically inhibits 3-hydroxy-3methylglutaryl coenzyme A reductase" The journal of Antibiotics, 1980.

J. Wang, Z Lu, J Chi et al. "Multicenter clinical trial of the serum lipidlowering effects of a *Monascus purpureus* rice preparation from traditional Chinese medicine" 1997.

Gallagher J. C. et al. "The effects of soy isoflavone intake on bone metabolism in post menopausal women." SECOND INTERNATIONAL SYMPOSIUM ON THE ROLE OF SOY IN PREVENTING AND TREATING CHRONIC DISEASE, Sep. 15-18, 1996, Brussels, Belgium.

Messina M. et al. "Soyfoods, soybean isoflavones, and bone health: a brief." J. Ren. Nutr. 10, 63-68, 2000.

Kurzer C. et al. "Hormonal effects of soy isoflavones: studies in premenopausal and postmenopausal women." J. Nutr. 130, 660s-661 S, 2000.

Alekel D. L. et al. "Isoflavone-rich soy protein isolate attenuates bone loss in the lumbar spine of perimenopausal women." Am. J. Clin. Nutr. 72, 844-852, 2000.

Wangen K. E. et al. "Effects of soy isoflavones on markers of bone turnover in premenopausal and postmenopausal women." J. Clin. Endocrinol. Metab. 85, 3043-3048, 2000.

Kurzer M. S. et al. "Hormonal effects of soy. Premenopausal studies. Effects of dietary soy isoflavones on estrogen action in premenopausal women." SECOND INTERNATIONAL SYMPOSIUM ON THE ROLE OF SOY IN PREVENTING AND TREATING CHRONIC DISEASE. Sep. 15-18, 1996, Brussels, Belgium. Scientific program (Oral abstracts). lo Farmakalidis E. et al. "Oestrogenic potency of genistin and daidzin in mice." Food Chem. Toxicol. 23,741-745, 1985.

The invention claimed is:

1. A functional food composition comprising an edible flour, wherein said edible flour comprises: policosanols, isoflavones and vegetable statins, added thereto and further comprising phytosterols.

2. The functional food composition according to claim 1, wherein the edible flour is wheat flour.

3. The functional food composition according to claim 1, wherein said policosanols are present in a concentration that ranges from 0.01% to 0.1% by weight, relative to the total weight of the flour; said isoflavones are present in a concentration that ranges from 0.02% to 0.15% by weight, relative to the total weight of the flour; and said vegetable statins are present in a concentration that ranges from 0.005% to 0.15% by weight, relative to the total weight of the flour.

4. The functional food composition according to claim 1, wherein said policosanols comprise octacosanol contained in a *Saccharum officinarum* extract.

5. The functional food composition according to claim 1, wherein the concentration of said phytosterols ranges from 0.005% to 0.5% by weight, relative to the total weight of the flour.

6. The functional food composition according to claim 1, wherein said phytosterols are contained in a *Cyclanthera pedata* extract.

7. The functional food composition according to claim 1, further comprising coenzyme Q10.

8. The composition according to claim 7, wherein the concentration of said coenzyme Q10 ranges from 0.005% to 0.07% by weight, relative to the total weight of the flour.

9. The functional food composition according to claim 1, comprising a *Glycine max* seed extract.

10. The functional food composition according to claim 9, wherein the concentration of said *Glycine max* seed extract ranges from 0.1% to 2% by weight, relative to the total weight of the flour.

11. The functional food composition according to claim 1, comprising the yeast *Monascus purpureus* fermented on a substrate of *Oryza sativa*.

12. The functional food composition according to claim 11, wherein the concentration of said yeast *Monascus purpureus* fermented on a substrate of *Oryza sativa* ranges from 0.1% to 2% by weight, relative to the total weight of the flour.

13. The functional food composition according to claim 1, comprising a *Medicago sativa* extract.

14. The functional food composition according to claim 13, wherein the concentration of said *Medicago sativa* extract ranges from 0.01% to 0.3% by weight, relative to the total weight of the flour.

15. The functional food composition according to claim 1, comprising a *Cynaria scolymus* leaf extract.

16. The functional food composition according to claim 15, wherein the concentration of said *Cynaria scolymus* extract ranges from 0.1% to 5% by weight, relative to the total weight of the flour.

17. A pasta obtainable using the composition of claim 1, for use as an adjuvant in the stabilization of cholesterol and triglyceride levels.

18. The functional food composition according to claim 1, for use as an adjuvant in the stabilization of cholesterol and triglyceride levels.

19. A baked product obtainable using the composition of claim 1, for use as an adjuvant in the stabilization of cholesterol and triglyceride levels.

* * * * *